United States Patent
Fomina et al.

(10) Patent No.: US 9,810,688 B2
(45) Date of Patent: Nov. 7, 2017

(54) SMART GLASS SLIDE FOR MICROARRAYS

(71) Applicant: Robert Bosch GmbH, Stuttgart (DE)

(72) Inventors: Nadezda Fomina, Fremont, CA (US); Christopher Johnson, San Carlos, CA (US); Sam Kavusi, Menlo Park, CA (US); Habib Ahmad, Sunnyvale, CA (US)

(73) Assignee: ROBERT BOSCH GMBH, Stuttgart (DE)

( * ) Notice: Subject to any disclaimer, the term of this patent is extended or adjusted under 35 U.S.C. 154(b) by 0 days.

(21) Appl. No.: 13/834,126

(22) Filed: Mar. 15, 2013

(65) Prior Publication Data

US 2014/0274760 A1    Sep. 18, 2014

(51) Int. Cl.
  *G01N 33/543*   (2006.01)
  *C40B 60/00*    (2006.01)
  *C40B 30/04*    (2006.01)
  *C40B 40/10*    (2006.01)
  *G01N 27/327*   (2006.01)

(52) U.S. Cl.
  CPC ..... *G01N 33/5438* (2013.01); *G01N 27/3272* (2013.01)

(58) Field of Classification Search
  CPC .................................................. G01N 33/5438
  USPC .............................................................. 506/9
  See application file for complete search history.

(56) References Cited

U.S. PATENT DOCUMENTS

| | | | |
|---|---|---|---|
| 6,976,982 B2 * | 12/2005 | Santini et al. | 604/891.1 |
| 7,195,913 B2 * | 3/2007 | Guire et al. | 435/401 |
| 8,648,016 B2 * | 2/2014 | Kavusi et al. | 506/9 |
| 2003/0228523 A1 * | 12/2003 | DeLongchamp et al. | 429/306 |
| 2008/0305486 A1 * | 12/2008 | Tan et al. | 435/6 |
| 2009/0117551 A1 * | 5/2009 | Suzuki | B82Y 5/00 435/6.12 |
| 2010/0105035 A1 * | 4/2010 | Hashsham et al. | 435/6 |
| 2010/0116691 A1 * | 5/2010 | Papadimitrakopoulos et al. | 205/778 |
| 2010/0285601 A1 * | 11/2010 | Kong | G01N 33/54306 436/94 |
| 2010/0326703 A1 * | 12/2010 | Gilad | A61B 1/041 174/254 |
| 2011/0087315 A1 * | 4/2011 | Richardson-Burns et al. | 607/116 |
| 2011/0091870 A1 | 4/2011 | Lang et al. | |

(Continued)

FOREIGN PATENT DOCUMENTS

WO    WO 0111080 A1 *  2/2001

OTHER PUBLICATIONS

Anderson et al., A System for Multiplexed Direct Electrical Detection of DNA Synthesis, Sens Actuators B Chem., 2008, 129(1), 79-86.*

(Continued)

*Primary Examiner* — Amy M Bunker
(74) *Attorney, Agent, or Firm* — Gerard Messina

(57) ABSTRACT

Device for use in a biosensor comprising a multisite array of test sites, the device being useful for modulating the binding interactions between a (biomolecular) probe or detection agent and an analyte of interest from a biological by modulating the pH or ionic gradient near the electrodes in such biosensor. The device provides a biosensor which is more accurate, reliable and the results of which are more reproducible. Analytic methods for more accurately measuring an analyte of interest in a biological sample are also provided.

15 Claims, 3 Drawing Sheets

(56) References Cited

U.S. PATENT DOCUMENTS

| | | | | |
|---|---|---|---|---|
| 2011/0278258 A1* | 11/2011 | Kavusi | ............. | G01N 33/54306 216/20 |
| 2012/0222958 A1* | 9/2012 | Pourmand et al. | ............ | 204/451 |
| 2013/0334467 A1* | 12/2013 | Zhou et al. | ................... | 252/500 |
| 2014/0008244 A1* | 1/2014 | Kavusi | .................. | G01N 33/50 205/777.5 |

OTHER PUBLICATIONS

Bizzarri et al., Green Fluorescent Protein Based pH Indicators for In Vivo Use: A Review, Anal. Bioanal. Chem., 2009, 393, 1107-1122.*
Choi et al., Charge Trap in Self-Assembled Monolayer of Cytochrome b562-Green Fluorescent Protein Chimera, Current Applied Physics, 2006, 6, 760-765.*
Zhang, J., Protein-Protein Interactions in Salt Solutions, Intech, 2012, 359-377.*
Oshige et al., Immobilization of His-Tagged Proteins on Various Solid Surfaces Using NTA-Modified Chitosan, Open Journal of Polymer Chemistry, 2013, 3, 6-10.*
Crone et al., GFP-Based Biosensors, Intech, Chapter 1, State of the Art in Biosensors—General Aspects, 2013, 1-34.*
Publication Date for Crone et al., GFP-Based Biosensors, Intech, Chapter 1, State of the Art in Biosensors—General Aspectis, 2013, 1-34.*
Turner, Biosensors: Sense and Sensibility, Chem Soc Rev, 2013, 42(8), 3125-3638.*
Borgmann et al., Amperometric Biosensors, Advances in Electrochemical Science and Engineering, 2011, 1-84.*
Yotter et al., Sensor Technologies for Monitoring Metabolic Activity in Single Cells-Part I: Optical Methods, IEEE Sensors Journal, 2004, 4(4), 395-411.*
Anderson et al., A System for Multiplexed Direct Electrical Detection of DNA Synthesis, NIH Public Access, Author Manuscript, 2009, 1-16.*
Campbell et al., The Effect of pH on Green Fluorescent Protein: A Brief Review, Molceular Biology Today, 2001, 2(1), 1-4.*
International Search Report dated Jul. 29, 2014 of the corresponding International Application PCT/US2014/026250 filed Mar. 13, 2014.
Bazin, Damien et al., "Electrodeposition of Polymer Nanodots with Controlled Density and Their Reversible Functionalization by Polyhistidinc-Tag Proteins", Langmuir, vol. 28, No. 39, Oct. 2, 2012, pp. 13968-13975.
Oshige, Masahiko et al., "Immobilization of His-Tagged Proteins on Various Solid Surfaces Using NTA-Modified Chitosan", Open Journal of Polymer Chemistry, Feb. 1, 2013, pp. 6-10.
Choi, JW et al., "Charge trap in self-assembled monolayerof cytochrome b562-green fluorescent protein chimera", Current Applied Physics, North-Holland, Amsterdam, NL, vol. 6, No. 4, Jul. 1, 2006, pp. 760-765.
Korostynska, Olga et al., "Review on State-of-the-art in Polymer Based pH Sensors" Sensors, Jan. 1, 2007, pp. 3027-3042. Retrieved from the internet: URL: http://www.ncbi.nlm.nih.gov/pmc/articles/PMC3841878/pdf/sensors-07-03027.pdf.
U.S. Appl. No. 13/543,300, filed Jan. 9, 2014, Kavusi et al.

* cited by examiner

SMART GLASS SLIDE FOR MICROARRAYS

FIELD OF THE INVENTION

The invention relates to a device for use in microarrays in a biosensor and diagnostic methods for biomolecules using such biosensor comprising the device. Moreover, the invention relates to a method for accurately and reliably controlling a pH gradient near electrode surfaces for modulating biomolecular interactions in such biosensor.

BACKGROUND INFORMATION

Recently there has been an increased interest in predictive, preventative, and particularly personalized medicine which requires diagnostic tests with higher fidelity, e.g., sensitivity and specificity. Multiplexed measurement platforms, e.g., protein arrays currently used in research, are among the promising diagnostics technologies for the near future. The samples in these tests can be human body fluids such as blood, serum, saliva, biological cells, urine, or other biomolecules but can also be consumables such as milk, baby food, or water. Within this field there is a growing need for low-cost, multiplexed tests for biomolecules such as nucleic acids, proteins, and also small molecules. Achieving the sensitivity and specificity needed in such tests is not without difficult challenges. Combining these tests with integrated electronics and using CMOS technology has provided solutions to some of the challenges.

The two main limitations in a detection assay include sensitivity and cross-reactivity. Both of these factors affect the minimum detectable concentration and therefore the diagnostic error rate. The sensitivity in such tests is generally limited by label detection accuracy, association factor of the probe-analyte pair (for example an antibody-antigen pair), and the effective density of probe molecule (for example probe antibody) on the surface. Other molecules in the biological sample can also affect the minimum detectable concentration by binding to the probe molecule (for example the primary antibody), or by physisorption of the analyte to the surface at the test site. The detection agent (for example a secondary antibody) may also physisorb to the surface causing an increase in the background signal. Solving the cross-reactivity and background problem can take a significant amount of time in the assay development of a new test and increases the cost and complexity of the overall test. The assay is typically optimized by finding the best reagents and conditions and also by manufacturing the most specific probe molecule (for example antibody). This results in a long development time, the infeasibility of tests in some cases, and a higher manufacturing cost. For example a typical development of an ELISA assay requires several scientists working for more than a year finding the correct antibody as part of the assay development. Cross-reactivity of the proteins may be the source of the failure of such an effort.

A biosensor providing a multiple site testing platform was thought to provide a solution to some of the above described limitations in assay development. US Published Patent Application US 2011/0091870 describes such biosensor having multiple sites that could be subjected to different reaction conditions to modulate the binding of the biomolecular analyte (for example proteins) to the probe molecule. For example the signal detected in a biosensor having four sites also can have several components, e.g. four. These four terms may correspond to the concentration of the biomarker of interest, concentration of interfering analytes in the sample that bind non-specifically to primary antibody (probe molecule) sites and prevent the biomarker to bind, concentration of interfering analytes in the sample that form a sandwich and produce wrong signal, and finally the concentration of interfering analytes in the sample that physisorb to the surface and produce wrong signal. Each term is also proportional to a binding efficiency factor, $\alpha_{ij}$, which is a function of the molecule affinities and other assay conditions, e.g., mass transport. By controlling the condition at each site separately, different sites will have different efficiency factors. Accurate measurement of the signal at each site will result in multiple equations and multiple unknowns for example, $$\begin{cases} S_1 = \alpha_{11}C_{an} - \alpha_{12}C_{j1} + \alpha_{13}C_{j2} + \alpha_{14}C_{j3} \\ S_2 = \alpha_{21}C_{an} - \alpha_{22}C_{j1} + \alpha_{23}C_{j2} + \alpha_{24}C_{j3} \\ S_3 = \alpha_{31}C_{an} - \alpha_{32}C_{j1} + \alpha_{33}C_{j2} + \alpha_{34}C_{j3} \\ S_4 = \alpha_{41}C_{an} - \alpha_{42}C_{j1} + \alpha_{43}C_{j2} + \alpha_{44}C_{j3} \end{cases} \Rightarrow C_{an}$$

where $C_{an}$ corresponds to the targeted biomolecular analyte concentration and $C_{j1}$, $C_{j2}$, $C_{j3}$ correspond to the total concentration of molecules which result in different terms in background signal.

Accurate and precise control of the assay conditions at different sites to generate large changes in the binding efficiency factors is important in the performance of such biosensor as a detection system for a biomolecular analyte of interest. In co-pending U.S. application Ser. No. 13/543,300 (the content of which is incorporated herein by reference in its entirety) such biosensors and such methods are described that can be readily integrated with a CMOS, electrode array, or TFT based setup to generate large change in binding efficiencies between test sites in a biosensor having an array of multiple test sites. In order to accurately measure the biomolecular analyte of interest the biosensor requires a high degree of reliability and reproducibility. Variations in the modulation of the local pH due to repeated use of the biosensor and variations between subsequent measurements may decrease the accuracy of the determination of the biomolecular analyte of interest by such biosensor. As such the modulation of the pH at each site of the multisite array of the biosensor needs to be accurately controlled and variations in such pH modulation need to be corrected. Therefore, there is a need for a biosensor in which the pH can be accurately, reliably, and reproducibly controlled at each of the multisite array test sites.

SUMMARY OF THE INVENTION

Herein provided are devices and methods for accurately, reliably and reproducibly controlling the pH that can be integrated with for example a CMOS, electrode array, or TFT based biosensor having an array of multiple test sites. In particular, the current application provides methods to reliably and reproducibly modulate the pH or ionic concentration near electrode surfaces of such biosensors in order to modulate the biomolecular interactions between a probe biomolecule and a biomolecular analyte of interest. The device described herein can be used in a biosensor as described in co-pending application Ser. No. 13/543,300 in order to repeatedly determine a biomolecular analyte of interest in a sample while maintaining a high degree of accuracy of the biosensor.

In one embodiment there is provided a device for use in a biosensor having a multisite array of test sites, the device comprising:
 (a) a transparent support substrate supporting one or more electrodes; and
 (b) a biomolecular interface layer having immobilized pH sensitive Fluorescent Protein and one or more immobilized probes thereon.

In another embodiment there is provided biosensor comprising the device comprising:
 (a) a transparent support substrate supporting one or more electrodes; and
 (b) a biomolecular interface layer having immobilized pH sensitive Fluorescent Protein and one or more immobilized probes thereon.

In another embodiment there is provided a method of modulating the pH or ionic concentration in a biosensor, the method comprising:
 a) providing a biosensor comprising a multisite array of test sites in which the conditions for interacting with a biomolecule analyte can be varied independently, the biosensor having a device comprising a transparent support substrate supporting one or more electrodes, and a biomolecular interface layer having immobilized pH sensitive Fluorescent Protein and one or more immobilized probes thereon; and
 b) reacting at the one or more electrodes an electrochemically active agent in an aqueous solution to produce H+ ion or OH− ions.

In yet another embodiment there is provided a method for detecting a biomolecule analyte in a biological sample, the method comprising:
 a) providing a biosensor comprising a multisite array of test sites in which the conditions for interacting with a biomolecule analyte can be varied independently, the biosensor having a device comprising a transparent support substrate supporting one or more electrodes and a biomolecular interface layer having immobilized pH sensitive Fluorescent Protein and one or more immobilized probes thereon, and at each test site having an aqueous solution comprising a dilute phosphate buffer and an electrochemically active agent;
 b) at each test site electrochemically reacting the electrochemically active agent in an aqueous solution to produce H+ ion or OH− ions, thereby modulating and controlling the pH at each test site;
 c) adding a biological sample to each test site; and
 d) detecting the biomolecule analyte in each test site,
wherein the amounts of electrochemically active agent and the electrochemical reaction are varied between test sites in a subset array of test sites in order to obtain sets of test sites in which the pH or ionic concentration near electrode surfaces in the test sites varies, and wherein the pH at each test site is determined by the fluorescence intensity of the pH sensitive Fluorescent Protein.

DETAILED DESCRIPTION

Methods to modulate the pH in a biosensor having a multisite array of test sites are described in co-pending U.S. patent application Ser. No. 13/543,300. When used in a biosensor the accuracy, reliability and reproducibility of the modulation of the pH at each test site is important. However the modulation of the pH at each test site may vary between subsequent uses. In order to accurately determine the amount of a biomolecular analyte of interest in a sample using the biosensor and method described in the aforementioned co-pending U.S. patent application Ser. No. 13/543, 300 the pH at each test site needs to be accurately modulated or controlled. The device provided herein allows for accurate determination and control of the pH at each test site in such biosensor, the device comprising:
 (a) a transparent support substrate supporting one or more electrodes; and
 (b) a biomolecular interface layer having immobilized pH sensitive Fluorescent Protein and one or more immobilized probes thereon.

The transparent support substrate in the device described herein is preferably a glass or plastic substrate but also be any other transparent non-glass substrate.

Figure 2:
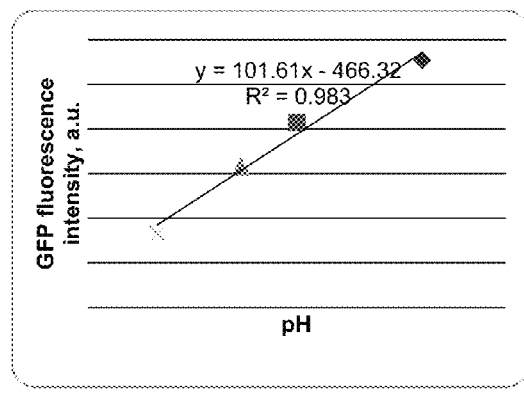
FIG. 2: shows the change in the fluorescence intensity of GFP covalently bound to the PEG-coated ITO in response to the change in solution pH. The solution pH was adjusted by adding HCl to a dilute phosphate buffer (pH 7.4).

The immobilized pH sensitive fluorescent protein allows for sensing the pH at an electrode once the electrode (working electrode) causes modulation of the pH at a particular test site such as a test site in a multisite array. The fluorescence intensity of the fluorescent protein changes due to modulation of the pH. The change in fluorescence intensity of the fluorescent protein is proportional to the change in the pH (there is a linear relationship between the pH and the fluorescence intensity). Therefore, as is also shown in FIG. 2, the pH value at each location at any time when the biosensor is in use can be readily obtained by correlating the fluorescence intensity of the fluorescent protein with the pH. An accurate calibration of the correlation between pH and fluorescence intensity may be carried out before or during use of the biosensor. When the calibration is carried out during use of the biosensor one or more test sites within a multisite array may be dedicated to calibration of the fluorescence intensity to pH correlation. When the pH is no longer modulated at such test site by the electrode (working electrode) the fluorescence intensity of the immobilized fluorescent protein reverts back to its intensity before a current was applied through the electrode.

Figure 4:
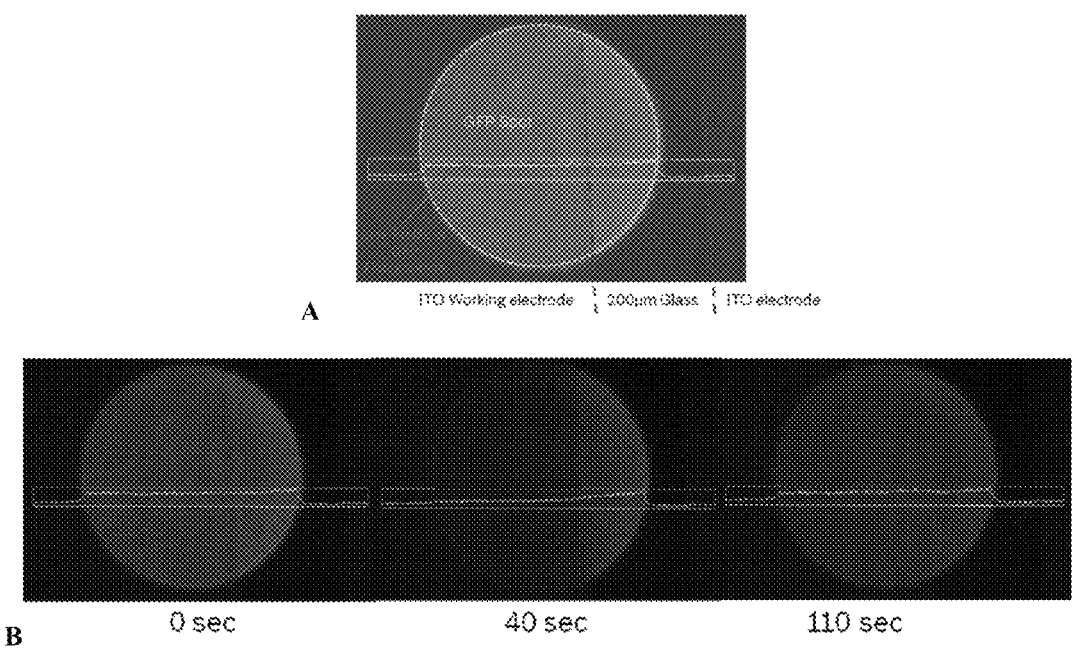
FIG. 4: illustrates the visual changes in the GFP spot before, during and after pH modulation experiment. A, the profile of fluorescence intensity across the spot is shown. B, the changes in the GFP spot fluorescence intensity are shown before (0 sec), during (40 sec), and after (110 sec) applying a current through an electrode.
Figure 5:
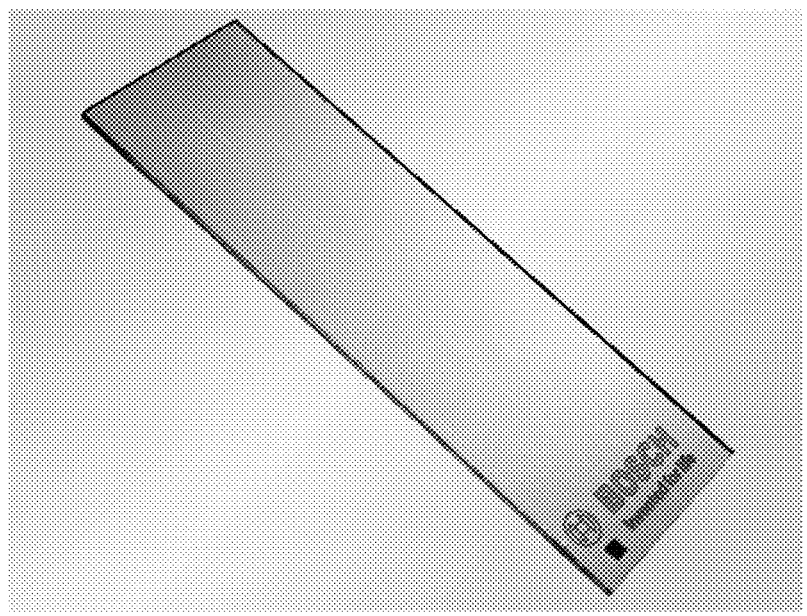
FIG. 5: shows a glass slide with an ASIC chip interfaced to transparent ITO electrodes.

Preferably, the immobilized fluorescent protein is selected from an immobilized green fluorescent protein, an immobilized yellow fluorescent protein, and an immobilized cyan fluorescent protein. More preferably, the immobilized fluorescent protein is immobilized Green Fluorescent Protein (GFP). In an alternative embodiment immobilized pH sensitive dyes may be used on the transparent support substrate instead of an immobilized pH sensitive fluorescent protein. In a multisite array of test sites in a biosensor the immobilized fluorescent protein covers on the substrate an area that is also covered by an electrode and an area that is not covered with an electrode. The electrode covered by the immobilized fluorescent protein is either a working electrode or a counter electrode. Preferably, the immobilized fluorescent protein is applied onto the substrate as distinct spots, wherein each spot overlaps with only one test site and an area not covered by an electrode as shown in FIG. 4A. The presence of fluorescent protein on an area that is not covered by an electrode allows for the determination, within the biosensor, of fluorescence intensity when the pH is not modulated by the electrode. This fluorescence intensity can be used as a standard and control in determining whether, after ceasing modulation of the pH by an electrode the fluorescence intensity will revert back to its original intensity. Accordingly, in a method for detecting a biomolecular analyte in a biological using the device, the fluorescent protein not located on or near an electrode can be used as an internal reference for signal normalization.

The device includes one or more counter electrodes and one or more working electrodes. In the device one or more electrodes can be arranged in a multisite array, each site of the multisite array comprising a working electrode and/or counter electrode. The electrodes can be any electrode suitable in a biosensor for example indium tin oxide (ITO), gold, or silver electrodes. In a preferred embodiment the electrodes in the device are indium tin oxide (ITO) electrodes. In an alternative embodiment the working electrode is an indium tin oxide electrode and the counter electrode(s) is selected from an indium oxide electrode, a gold electrode, a platinum electrode, a silver electrode, and a carbon electrode.

The electrodes in the device may be used either for modulating the pH or as sensing electrodes or both. In the device or biosensor using the device, the one or more electrodes are connected to an electronic board via pogo-pins, a chip on foil via z-axis adhesive, or a chip on the substrate. The electronic board or chip are powered by a printed battery, a small battery bound to the substrate, a magnetically coupled power transfer using coils on the substrate, or a rf-coupled power transfer using coils on the substrate.

The biomolecular probe is attached or immobilized onto the support and/or electrode(s) within a biomolecular interface layer. The biomolecular layer includes a layer of immobilized polymers, preferably a silane immobilized polyethylene glycol (PEG). Surface-immobilized polyethylene glycol (PEG) can be used to prevent non-specific adsorption of biomolecular analytes onto surfaces. At least a portion of the surface-immobilized PEG can comprise terminal functional groups such as N-hydroxysuccinimide (NHS) ester, maleimide, alkynes, azides, streptavidin or biotin that are capable of conjugating. The biomolecular probe may be immobilized by conjugating with the surface-immobilized PEG. It is important that during operation of the device the change of the pH does not impair the covalent binding of for example the PEG onto the surface of a solid support, or the linker that conjugated the biomolecular probe to the PEG.

A suitable biomolecular probe can be a carbohydrate, a protein, a glycoprotein, a glycoconjugate, a nucleic acid, a cell, or a ligand for which the analyte of interest has a specific affinity. Such probe can for example be an antibody, an antibody fragment, a peptide, an oligonucleotide, a DDA oligonucleotide, a RNA oligonucleotide, a lipid, a lectin that binds with glycoproteins and glycolipids on the surface of a cell, a sugar, an agonist, or antagonist. In a specific example, the biomolecular probe is a protein antibody which interacts with an antigen that is present for example in a biological sample, the antigen being a biomolecular analyte of interest.

A biosensor comprising the device provided herein can be used in an analytical method for determining a biomolecular analyte of interest in a biological sample, which can be for example a protein, such as an antigen or enzyme or peptide, a whole cell, components of a cell membrane, a nucleic acid, such as DNA or RNA, or a DNA oligonucleotide, or a RNA oligonucleotide.

In such method a local pH or ionic concentration gradient can be obtained at various test sites in a multisite array biosensor. The variation of the local pH and/or ionic concentration gradient at the electrode, and in particular in the vicinity of the (biomolecular) probe in a biomolecular interface layer, over subsets of the multisite array of the biosensor, allows for modulating the binding efficiency of the (biomolecular) probe and an analyte to be tested from a biological sample. The analyte of interest, when bound to the (biomolecular) probe, can be then detected using a detection agent, such as for example a labeled secondary antibody. The modulation of binding efficiencies in a subset of a multisite array provides a method for the accurate determination of such analyte of interest.

The device preferably a multisite array of test sites within a biosensor, which multisite array is for example described in US 2011/0091870. Such multisite array preferably includes a number of different subarrays/subsets of test sites. Each test sites represents a site for performing an analysis of a (biomolecular) analyte from a biological sample through the detection of the (biomolecular) analyte using a (biomolecular) probe. The analytical conditions in each test site in each of the subarrays/subsets may be varied to obtain a collection of varied signals that will result in multiple equations and multiple unknowns from which the concentration of the (biomolecular) analyte can be determined in order to obtain an accurate measurement of the (biomolecular) analyte.

The multiple unknowns in the obtained varied signals each includes a term that is proportional to a binding efficiency factor, $\alpha_{ij}$, and the concentrations of the various molecules in the biological sample binding that are detected at the test site. The multiple equations with multiple unknowns may be represented for example as follows, $$\begin{cases} S_1 = \alpha_{11}C_{an} - \alpha_{12}C_{j1} + \alpha_{13}C_{j2} + \alpha_{14}C_{j3} \\ S_2 = \alpha_{21}C_{an} - \alpha_{22}C_{j1} + \alpha_{23}C_{j2} + \alpha_{24}C_{j3} \\ S_3 = \alpha_{31}C_{an} - \alpha_{32}C_{j1} + \alpha_{33}C_{j2} + \alpha_{34}C_{j3} \\ S_4 = \alpha_{41}C_{an} - \alpha_{42}C_{j1} + \alpha_{43}C_{j2} + \alpha_{44}C_{j3} \end{cases} \Rightarrow C_{an}$$

where $C_{an}$ corresponds to the targeted biomolecular analyte concentration and $C_{j1}$, $C_{j2}$, $C_{j3}$ correspond to the total concentration of molecules which result in different terms in background signal, from which collection of multiple equations the concentration of the targeted biomolecular analyte can be determined.

The number of subarrays/subsets, as well as the number of test sites within each subarray/subset may be varied, as needed to obtain such accurate measurement of the analyte. Some of these analytical conditions include parameters such as for example temperature, shear stress, and pressure. For example the temperature of the aqueous solution in which the biomolecular probe and analyte of interest in the biological sample interact can be varied using the electromagnetic heat at the test site. Another important condition for the interaction between the biomolecular probe and the analyte of interest is the pH or ionic concentration.

The device provided herein and used in a biosensor comprises such array of multiple test sites in solution in order to modulate the pH at each test site and to determine the presence and concentration of a biomolecular analyte of interest in a biological sample. In such use the device is in contact with an aqueous solution comprising a phosphate buffer, preferably a diluted phosphate buffer which preferably has a concentration of 0.1 mM to 100 mM. In a preferred embodiment the pH of the diluted phosphate buffer is between 5 and 8, preferably between 7 and 8, and more preferably between 7 and 7.5.

The aqueous solution may further comprise one or more additional electrolytes, such as for example sodium sulfate, or any other suitable strong electrolyte. Preferably, the additional electrolyte is selected from sodium sulfate, sodium or potassium chloride, sodium or potassium bromide, sodium or potassium iodide, sodium or potassium perchlorate, sodium or potassium nitrate, tetraalkylammonium bromide and tetraalkylammonium iodide. Buffer-inhibitors may also be used in the aqueous solution. Suitable buffer inhibitors may be selected from poly(allylamine hydrochloride), poly(diallyldimethyl ammonium chloride), poly(vinylpyrroldone), poly(ethyleneimine), poly(vinylamine), poly(4-vinylpyridine) and tris(2-carboxyethyl)phosphine hydrochloride. When used in a method to modulate the pH such as described in co-pending U.S. patent application Ser. No. 13/543,300 the aqueous solution preferably also comprises a water-miscible organic co-solvent selected from the groups consisting of acetonitrile, dimethyl sulfoxide (DMSO), dimethyl formamide (DMF), N,N-dimethyl acetamide (DMAc), and mixtures thereof.

In such method the pH modulation on the device provided herein can be carried out using an electrochemically active agent. Suitable electrochemically active agents include dopamine hydrochloride, ascorbic acid, phenol and derivatives, benzoquinones and derivatives, for example, 2,5-dihydroxy-1,4-benzoquinone, 2,3,5,6-tetrahydroxy-1,4-benzoquinone and 2,6-dichloroquinone-4-chloroimide; naphthoquinones and derivatives, for example, hydroxy-1,4-naphthoquinone, 5,8-dihydroxy-1,4-naphthoquinone, and potassium 1,4-naphthoquinone-2-sulfonate; and 9,10-anthraquinone and derivatives, for example, sodium anthraquinone-2-carboxylate, potassium 9,10-anthraquinone-2,6-disulfonate. Preferably the concentration of the electrochemically active agent in the aqueous solution is from 1 nM to 100 mM.

In another embodiment is provided a method of modulating the pH using the device in a biosensor. The method of modulating the pH or ionic concentration in a biosensor comprises:
 a) providing a biosensor including one or more devices as described herein comprising a multisite array of test sites in which the conditions for interacting with a biomolecule analyte can be varied independently; and
 b) reacting at the one or more electrodes an electrochemically active agent in an aqueous solution to produce H+ ion or OH− ions.

In the method the concentration of the electrochemically active agent in the aqueous solution is preferably from 1 nM to 100 mM.

In a method of modulating the pH in a biosensor using the device described herein the electrochemically active agent may be electro-oxidized or electro-reduced at an electrode potential in the range of −2V to +2V. Preferably the electrode potential is in the range of −1V to +1V, even more preferably the electrode potential is in the range of −0.5V to +0.5V. The voltage required to drive the redox reaction can be used as a real time feedback method to monitor pH that is produced at the electrode surface.

Modulation of the pH or ionic concentration on a device in a biosensor described herein by electrochemical reaction at the one or more electrode may be carried out in a galvanostatic mode or potentiostatic mode. In addition, any type of electrical pulse may be applied on the electrodes of the device in the method for modulating the pH. Such pulse may be in the form of an annealing pulse and may vary by pulse frequency, pulse width, and pulse shape. In an annealing pulse a sufficient voltage is applied to change the pH to such that non-covently bound molecules from the biological sample are removed from the device in the biosensor. Such annealing pulse eliminates or reduces the need for washing the substrate following first contact with a sample in order to remove non-covalently bound material. Another advantage is that the annealing pulse may be more efficient to remove such non-covalently bound material from the device than a simple washing. A preferred pulse width for modulating the pH is in the range of 1 nanosecond to 60 minutes.

In another embodiment there is provided an analytical method of using the device described herein in a biosensor to determine the presence and/or concentration of a biomolecular analyte of interest in a biological sample. This analytical method comprises
 a) providing a biosensor comprising a multisite array of test sites in which the conditions for interacting with a biomolecule analyte can be varied independently, the biosensor having a device comprising a transparent support substrate supporting one or more electrodes and a biomolecular interface layer having immobilized pH sensitive Fluorescent Protein and one or more immobilized probes thereon, and at each test site having an aqueous solution comprising a dilute phosphate buffer and an electrochemically active agent;
 b) at each test site electrochemically reacting the electrochemically active agent in an aqueous solution to produce H+ ion or OH− ions, thereby modulating and controlling the pH at each test site;
 c) adding a biological sample to each test site; and
 d) detecting the biomolecule analyte in each test site,
wherein the amounts of electrochemically active agent and the electrochemical reaction are varied between test sites in a subset array of test sites in order to obtain sets of test sites in which the pH or ionic concentration near electrode surfaces in the test sites varies, and wherein the pH at each test site is determined by the fluorescence intensity of the pH sensitive Fluorescent Protein.

The biomolecular analyte can be detected using any suitable detection method. Known detection methods of such analyte include luminescence, fluorescence, colorimetric methods, electrochemical methods, impedance measurements, or magnetic induction measurements. In various of such methods the analyte binds to the immobilized biomolecular probe and a detection agent such as for example a secondary labeled probe that specifically binds to the analyte, bound to the immobilized probe, is introduced. This detection agent or secondary labeled probe gives rise to a detectable signal such as for example luminescence or fluorescence.

Figure 1:
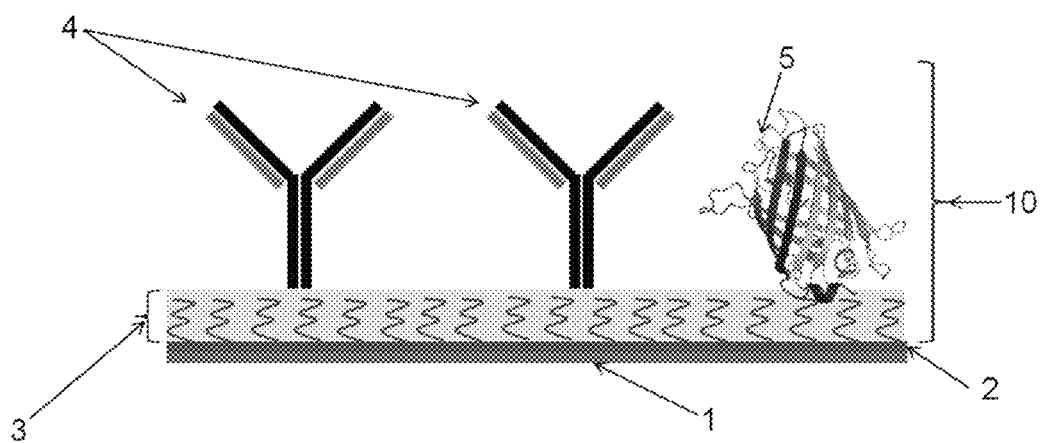
FIG. 1: Illustration of a substrate (glass or plastic) (1) with an array of electrodes (2) onto which a biomolecular interface layer (10) is applied which include fluorescence protein (such as Green Fluorescence Protein (GFP)) spots (5), and immobilized probes (4), immobilized using a polyethylene glycol (PEG) linker (3).

The following description is an illustration of a specific embodiment which may be modified within the scope of the description as would be understood from the prevailing knowledge. FIG. 1, shows a side view of a part of the device which includes a substrate (1) from glass or plastic. One or more electrodes (2) are covered onto the substrate (1) which is also covered with a biomolecular interface layer (10). The biomolecular interface layer (10) comprises immobilized PEG (3), immobilized probe (4) and immobilized pH sensitive fluorescent protein in the form of Green Fluorescent Protein spots (5). The GFP spots (5) overlap with an electrode (2) and an area that is not covered by an electrode. The electrodes (2) and the GFP spots (5) are arranged in a multisite array so as to provide multiple test sites on the device.

The following are examples which illustrate specific methods without the intention to be limiting in any manner. The examples may be modified within the scope of the description as would be understood from the prevailing knowledge.

EXAMPLES

Electrochemical Modulation of pH as Monitored by Fluorescence Intensity with Green Fluorescence Protein (GFP)

Electrode material used: The electrode material was indium tin oxide. The fluorescent protein used is GFP immobilized on a glass substrate which includes an array of electrodes. The GFP is applied as spots, each spot covers an area that overlaps with one electrode and an area that is not overlapping with an electrode.

Figure 3:
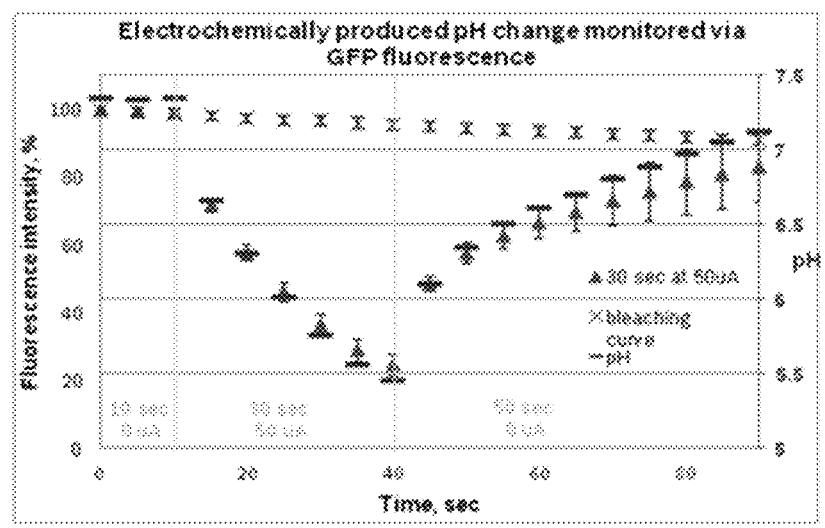
FIG. 3: shows the pH change at the surface of ITO working electrode generated via current-driven oxidation of a redox active molecule, 2-methyl-1,4-dihydroquinone, in diluted phosphate buffer (pH=7.4) containing 0.1M $Na_2SO_4$. After 10 seconds of induction, current (50 microamps) was applied for 30 second, which resulted in a drop of solution pH to 5.5, as was observed by a change in GFP fluorescence intensity (FIG. 2 is used as calibration curve to assess the pH values). After current was turned off, the pH recovered to neutral value within 50 seconds.

The pH change at the surface of ITO working electrode is generated via current-driven oxidation of a redox active molecule, 2-methyl-1,4-dihydroquinone, in diluted phosphate buffer (pH=7.4) containing 0.1M $Na_2SO_4$. After 10 seconds of induction, current (50 microamps) was applied for 30 second, which resulted in a drop of solution pH to 5.5, as was observed by a change in GFP fluorescence intensity. FIG. 2 is used as calibration curve to assess the pH values. After current was turned off, the pH recovered to neutral value within 50 seconds (as shown in FIGS. 3 and 4B).

What is claimed is:

1. A device for use in a biosensor, the device comprising a multisite array of test sites, the multisite array of test sites including:
   (1) a support substrate, wherein the support substrate is glass or plastic; and
   (2) a biomolecular interface layer that includes:
      (i) a layer of immobilized polyethylene glycol (PEG) that covers the support substrate;
      (ii) a plurality of Green Fluorescent Protein spots that are immobilized by attachment directly to the layer of immobilized PEG; and
      (iii) a plurality of immobilized probes immobilized by attachment directly to the layer of immobilized PEG, wherein the plurality of immobilized probes are selected from the group consisting of a protein, a peptide, an antibody, an antigen, a nucleic acid, and a cell; wherein:
   (a) each test site of the multisite array of test sites comprises:
      (i) a single Green Fluorescent Protein spot of the plurality of Green Fluorescent Protein spots;
      (ii) at least one working electrode that includes one or more counter-electrodes;
      (iii) a first area of the support substrate that supports, and is covered by, the at least one working electrode, wherein the device is configured to repeatedly modulate a pH of the first area of the support substrate with the at least one working electrode; and
      (iv) a second area of the support substrate;
   (b) the biomolecular interface layer is arranged such that, with respect to each test site of the multisite array of test sites:
      (i) a first portion of the single Green Fluorescent Protein spot covers the at least one working electrode that covers the first area of the support substrate; and
      (ii) a second portion of the single Green Fluorescent Protein spot covers the second area of the support substrate without any working electrodes arranged between the second area of the support substrate and the second portion of the single Green Fluorescent Protein spot that covers the second area of the support substrate; and
   (c) independently with respect to each test site of the multisite array of test sites:
      (i) the device is configured to repeatedly perform the following:
         (1) determine the pH level in the first area of the support substrate by detection of a fluorescence intensity of the first portion of the single Green Fluorescent Protein spot covering the at least one working electrode; and
         (2) determine the pH level in the second area of the support substrate by detection of a fluorescence intensity of the second portion of the single Green Fluorescent Protein spot covering the second area of the support substrate; and
      (ii) the pH level determined for the second area of the support substrate is a control by which the device is configured to determine when the pH level determined for the first area of the support substrate has reverted to a base level.

2. The device according to claim 1, wherein the at least one working electrode and the one or more counter-electrodes are selected from the group consisting of an indium tin oxide electrode, a gold electrode, a platinum electrode, a silver electrode, and a carbon electrode.

3. The device according to claim 2, wherein the at least one working electrode is an indium oxide electrode and the one or more counter-electrodes are selected from the group consisting of an indium tin oxide electrode, a gold electrode, a platinum electrode, a silver electrode, and a carbon electrode.

4. The device according to claim 1, further comprising an aqueous solution with which the support substrate is in contact.

5. The device according to claim 4, wherein the aqueous solution comprises a diluted phosphate buffer and wherein the pH of the aqueous solution is between pH=5 to pH=8.

6. The device according to claim 4, wherein the aqueous solution comprises electrolytes selected from the group consisting of sodium sulfate, sodium or potassium chloride, sodium or potassium bromide, sodium or potassium iodide, sodium or potassium perchlorate, sodium or potassium nitrate, tetraalkylammonium bromide, tetraalkylammonium iodide, and combinations thereof.

7. The device according to claim 4, wherein the aqueous solution comprises at least one soluble polymer selected from the group consisting of poly(allylamine hydrochloride), poly (diallyldimethyl ammonium chloride), poly(vinylpyrrolidone), poly(ethyleneimine), poly(vinylamine), poly(4-vinylpyridine), and tris(2-carboxyethyl)phosphine hydrochloride.

8. The device according to claim 4, wherein the aqueous solution comprises a water-miscible organic co-solvent selected from the group consisting of acetonitrile, dimethyl sulfoxide (DMSO), dimethylformamide (DMF), N,N-dimethyl acetamide (DMAc), and mixtures thereof.

9. The device according to claim 4, wherein the aqueous solution comprises an electrochemically active agent selected from the group consisting of dopamine hydrochloride, ascorbic acid, phenol, benzoquinones, naphthoquinones, and 9,10-anthraquinone.

10. The device according to claim 1, wherein the at least one working electrode and the one or more counter-electrodes are connected to an electronic board via pogo-pins.

11. The device according to claim 10, wherein the electronic board is powered by a power source selected from the group consisting of a printed battery, a small battery bound to the substrate, a magnetically coupled power transfer using coils on the substrate, and a radiofrequency (rf)-coupled power transfer using coils on the substrate.

12. The device according to claim 1, wherein the biosensor comprises a complementary metal-oxide-semiconductor (CMOS).

13. The device according to claim 1, wherein the at least one working electrode and the one or more counter-electrodes are connected to a chip on foil via z-axis adhesive or to a chip on the substrate.

14. The device according to claim 1, wherein the biosensor comprises a thin-film transistor (TFT) based system.

15. The device according to claim 13, wherein the chip is powered by a power source selected from the group consisting of a printed battery, a small battery bound to the substrate, a magnetically coupled power transfer using coils on the substrate, and a radiofrequency (rf)-coupled power transfer using coils on the substrate.

* * * * *